United States Patent
Parri et al.

[11] Patent Number: 5,622,648
[45] Date of Patent: *Apr. 22, 1997

[54] REACTIVE LIQUID CRYSTAL COMPOUNDS

[75] Inventors: Owain L. Parri; David Coates; Simon Greenfield; Ian Bonny, all of Dorset, Great Britain

[73] Assignee: Merck Patent Gesellschaft Mit Beschrankter Haftung, Darmstadt, Germany

[*] Notice: The portion of the term of this patent subsequent to Jun. 25, 2013, has been disclaimed.

[21] Appl. No.: 321,884

[22] Filed: Oct. 14, 1994

[30] Foreign Application Priority Data

Oct. 15, 1993 [EP] European Pat. Off. .............. 93116679

[51] Int. Cl.$^6$ .......................... C09K 19/12; C09K 19/20; C09K 19/34
[52] U.S. Cl. ................. 252/299.66; 252/299.01; 252/299.61; 252/299.67
[58] Field of Search ............... 252/299.01, 299.66, 252/299.67, 299.61; 359/106

[56] References Cited

U.S. PATENT DOCUMENTS

| | | | |
|---|---|---|---|
| 4,983,318 | 1/1991 | Matsumoto et al. | 252/299.01 |
| 5,188,760 | 2/1993 | Hikmet et al. | 252/299.01 |
| 5,210,630 | 5/1993 | Heyndericky et al. | 359/106 |
| 5,240,636 | 8/1993 | Doane et al. | 252/299.01 |
| 5,257,127 | 10/1993 | Hikmet | 359/328 |
| 5,332,520 | 7/1994 | Bach et al. | 252/299.01 |
| 5,354,498 | 10/1994 | Akashi et al. | 252/299.01 |
| 5,360,576 | 11/1994 | Blatter et al. | 252/299.61 |
| 5,372,745 | 12/1994 | Yoshinaga et al. | 252/299.01 |

FOREIGN PATENT DOCUMENTS

| | | |
|---|---|---|
| 293870 | 12/1988 | European Pat. Off. . |
| 484972 | 5/1992 | European Pat. Off. . |
| 501563 | 9/1992 | European Pat. Off. . |
| 94/08268 | 9/1993 | WIPO . |
| 93/22397 | 11/1993 | WIPO . |

OTHER PUBLICATIONS

Geibel, Kurt, "In Situ Photopolymerized, Oriented Liquid-Crystalline . . ." Advanced Meterials, 5, No. 2, Feb. (1993), pp. 107–109.

*Primary Examiner*—Richard D. Lovering
*Attorney, Agent, or Firm*—Millen, White, Zelano, & Branigan, P.C.

[57] ABSTRACT

Disclosed are liquid crystal compounds of formula I $$R^1-P-X-(A^1-Z^1)_n-A^2-R^2 \quad I$$

wherein
R is

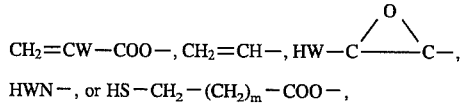

$HWN-$, or $HS-CH_2-(CH_2)_m-COO-$,

W is H, Cl or $C_{1-5}$-alkyl, and
m is 1–7,
P is $C_{1-12}$ alkylene, one or more $CH_2$ groups optionally being replaced by O,
X is $-O-$, $-S-$, $-COO-$, $-OCO-$ or a single bond,
$R^2$ is $C_{1-15}$-alkyl optionally substituted by halogen, one or more $CH_2$ groups optionally replaced by $-O-$, $-S-$, $-CO-$, $-O-CO-$, $-CO-O-$ or $-O-CO-O-$; $R^1-P-X$, CN, F, Cl or $-V-Q-T$,
V is $-O-$, $-S-$ or a single bond,
Q is $-CH_2-$, $-CHF-$, $-CF_2-$,
T is F or Cl,
n is 1 or 2,
$A^1$, $A^2$ are 1,4-phenylene optionally substituted by F, Cl, CN or $-W-C_rH_sF_{2r+1-s}$, or one of $A^1$ or $A^2$ is

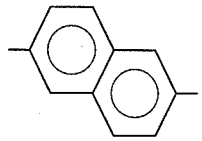

pyrimidine-2,5-diyl or pyrimidine-2,5 diyl,
$Z^1$ is $-CO-O-$, $-O-CO-$, $-CH_2CH_2-$ or a single bond,
r is 1 or 2,
s is 0, 1, 2, 3, 4, or 5,
W is a single bond, $-O-$, $-S-$ or $-CO-$,
with the provisos (i) that at least one of $A^1$ and $A^2$ is a 1,4-phenylene group which is mono-or polysubstituted by Cl, CN or $-W-C_rH_sF_{2r+1-s}$, said substituted 1,4-phenylene group optionally additionally substituted by one or more F-atoms, and (ii) that in case n=2 (a) only one of $Z^1$ is $-COO-$ or $-OCO-$ or (b) at least one of $A^1$ and $A^2$ is double substituted or (c) at least two of $A^1$ and $A^2$ are substituted.

8 Claims, No Drawings

REACTIVE LIQUID CRYSTAL COMPOUNDS

SUMMARY OF THE INVENTION

The invention relates to reactive liquid crystal compounds of formula I $$R^1\text{—}P\text{—}X\text{—}(A^1\text{—}Z^1)_n\text{—}A^2\text{—}R^2 \qquad I$$

wherein
$R_1$ is

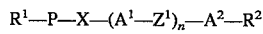

$CH_2=CW\text{—}COO\text{—}$, $CH_2=CH\text{—}$, $HW\text{—}C\overset{O}{\underset{\diagdown\diagup}{\phantom{XX}}}C\text{—}$, $HWN\text{—}$, or $HS\text{—}CH_2\text{—}(CH_2)_m\text{—}COO\text{—}$ with W being H, Cl or alkyl with 1–5 C atoms and m being 1–7,

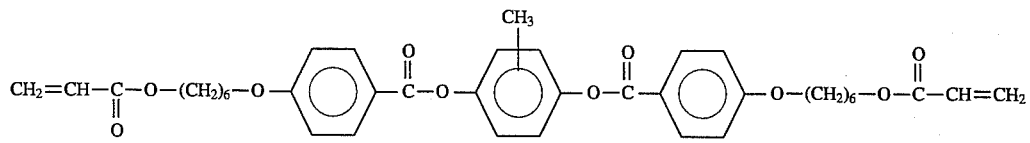

P is alkylene with up to 12 C atoms, it being also possible for one or more, e.g., up to 5, $CH_2$ groups to be replaced by O, X is —O—, —S—, —COO—, —OCO— or a single bond, $R^2$ is an alkyl radical with up to 15 C atoms which is unsubstituted, mono- or polysubstituted, e.g., up to perhalo substituted, by halogen, it being also possible for one or more, e.g., up to 5, $CH_2$ groups in these radicals to be replaced, in each case independently of one another, by —O—, —S—, —CO—, —O—CO—, —CO—O— or —O—CO—O— in such a manner that oxygen atoms are not directly linked to one another, or alternatively $R^2$ has one of the meanings given for $R^1$—P—X or is CN, F, Cl or —V—Q—T wherein V is —O—, —S— or a single bond, Q is —$CH_2$—, —CHF—, —$CF_2$—, and T is F or Cl, n is 1 or 2, $A^1$, $A^2$ are independently from each other 1,4-phenylene which is unsubstituted or mono- or polysubstituted (i.e., 2 to 4 times) by F, Cl, CN or —W—$C_rH_sF_{2r+1-s}$, and one of $A^1$ and $A^2$ may also denote

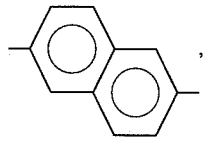

pyridine 2,5-diyl or pyrimidine-2,5-diyl, $Z^1$ is independently from each other —CO—O—, —O—CO—, —$CH_2CH_2$— or a single bond, r is 1 or 2, s is 0, 1, 2, 3, 4, or 5, W is a single bond, —O—, —S— or —CO—, wherein if n=2 both the moieties $A^1$ as well as both the moieties $Z^1$ have the meaning given above, independently from each other, with the provisos (i) that at least one of $A^1$ and $A^2$ is 1,4-phenylene which is mono-or polysubstituted by Cl, CN or —W—$C_rH_sF_{2r+1-s}$, it also being possible for this substituted 1,4-phenylene group to be additionally substituted by one or more F-atoms, and (ii) that in case n=2 (a) only one of $Z^1$ is —COO— or —OCO— or (b) at least one of $A^1$ and $A^2$ is double substituted or (c) at least two of $A^1$ and $A^2$ are substituted.

The invention furthermore relates to the preparation of such compounds and to their use in electrooptical scattering systems and for the preparation of oriented liquid crystal polymers.

Reactive liquid crystal compounds can be polymerized in situ, while in their liquid crystal phase, to give highly crosslinked anisotropic films which can be used, for example, as polarizing beam splitters (see, for example, EP 0,428,213). Reactive liquid crystal compounds have furthermore been proposed for electrooptical scattering systems (see, for example, EP 0,451,905).

Reactive liquid crystal diesters of formula which are laterally substituted by a methyl group are mentioned in EP 0,331,233, equivalent to U.S. Pat. No. 4,983,479. These reactive liquid crystalline compounds often exhibit, however, rather high melting points and disadvantageous values of birefringence.

In view of the broad range of applications of reactive liquid crystal compounds it was desirable to have available further compounds of this type which fulfill the various requirements such as a reasonably low melting point, a high birefringence, a broad mesogenic range and preferably an enantiotropic nematic range to a high degree.

It was an object of the present invention to provide new reactive liquid crystalline compounds with advantageous properties thus extending the pool of reactive liquid crystal compounds available to the expert. Other objects of the present invention can be taken from the following detailed specification.

The present invention thus relates to reactive liquid crystal compounds of formula I and to their use in electrooptical systems of scattering type and for the preparation of oriented liquid crystal polymers. The invention furthermore relates to the preparation of compounds according to formula I.

Above and below, the term reactive liquid crystalline compounds refers to reactive rod-like molecules of formula I or other rod-like reactive compounds which may be enantiotropic, monotropic or isotropic, preferably, however, enentiotropic or monotropic.

In the compounds of formula I, $A^1$ and $A^2$ can be independently from each other an unsubstituted or a substituted 1,4-phenylene group of formula

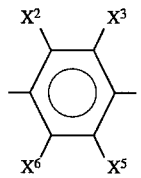

$X^2$, $X^3$, $X^5$ and $X^6$ can be independently from each other H, F, Cl, CN or —W—$C_rH_sF_{2r+1-s}$.

In the following, for the sake of simplicity, the following notation will be used:

Phe.2 $X^2$ 3 $X^3$ 5 $X^5$ 6 $X^6$ is a 1,4-phenylene group carrying in 2-position the group $X^2$, in 3-position the group $X^3$ etc.; in case $X^2$, $X^3$, $X^5$ and/or $X^6$ denote H, this will not be specified in above notation, i.e., only true substitutions will be listed. Thus Phe, for example, is an unsubstituted 1,4 phenylene group while Phe.2F 5 Cl is a 2-fluoro-5-chloro-1,4-phenylene group. Furthermore, Pyr is pyrimidine-2,5-diyl, Pyd is pyridine-2,5-diyl and Nap is a naphthalene-2,6-diyl group. The notation Pyr and Pyd in each case include the 2 possible positional isomers.

The compounds according to formula I comprise 2- and 3-ring compounds (n=1 or 2) of formula I2 and I3:

$$R^1—P—X—A^1—Z^1—A^2—R^2 \quad \text{I2}$$

$$R^1—P—X—A^1—Z^1—A^1—Z^1—A^2—R^2 \quad \text{I3}$$

In the 3-ring compounds of formula I3, the ring groups A1 can be chosen independently from each other.

Compounds according to formula I which are laterally monofluorinated often exhibit smectic phases and are not covered by the present invention. Contrary to this, compounds according to formula I which are laterally mono-substituted by —Cl, —CN or —W—$C_rH_{2r+1-s}$ and, in particular, by —Cl, —$CH_3$, —O—$CH_3$, —$CF_3$, —$OCF_3$, —$CH_2F$, —$OCH_2F$, —$CHF_2$, —$OCHF_2$, —$C_2H_5$, —S—$CH_3$, —S—$CF_3$ are characterized by advantageous properties and the tendency to form smectic phases is considerably reduced.

Compounds according to formula I which are laterally di- or higher substituted by —F, —Cl, —CN and/or —W—$C_rH_{2r+1-s}$ and, in particular, by —F, —Cl, —CN, —$CH_3$, —$OCH_3$, —$CF_3$ and/or —$OCF_3$ are furthermore preferred. This substitution pattern distinctly suppresses smectic phases and promotes formation of the nematic phase.

3-ring compounds according to formula I wherein both bridging groups $Z^1$ are —COO— and/or —OCO— are often characterized by an insufficient stability and these compounds are not covered by the present invention. Especially preferred is a smaller group of 2-ring compounds exhibiting the following structures for —$A^1$—$Z^1$—$A^2$—:

| | |
|---|---|
| —Phe.2$CH_3$—Phe— | I2-1 |
| —Phe.3$CH_3$—Phe— | I2-2 |
| —Phe.2Cl—Phe— | I2-3 |
| —Phe.3Cl—Phe— | I2-4 |
| —Phe.2CN—Phe— | I2-5 |
| —Phe.3CN—Phe— | I2-6 |
| —Phe.2Cl3Cl—Phe— | I2-7 |
| —Phe.2Cl3F—Phe— | I2-8 |
| —Phe.2O$CH_3$—Phe— | I2-9 |
| —Phe.3O$CH_3$—Phe— | I2-10 |
| —Phe.2$C_2H_5$—Phe— | I2-11 |
| —Phe.3$C_2H_5$—Phe— | I2-12 |
| —Phe.2$CF_3$—Phe— | I2-13 |
| —Phe.3$CF_3$—Phe— | I2-14 |
| —Phe.2$CH_3$—Phe.2$CH_3$— | I2-15 |
| —Phe.2$CH_3$—Phe.3$CH_3$— | I2-16 |
| —Phe.2$CH_3$—Phe.2F— | I2-17 |
| —Phe.2$CH_3$—Phe.3F— | I2-18 |
| —Phe.2$CH_3$—Nap— | I2-19 |
| —Phe.2Cl—Nap— | I2-20 |
| —Phe.3$CH_3$—Nap— | I2-21 |
| —Phe.3Cl—Nap— | I2-22 |
| —Phe.2$CH_3$—Pyr— | I2-23 |
| —Phe.2Cl—Pyr— | I2-24 |
| —Phe.2$CH_3$—Pyd— | I2-25 |
| —Phe.2Cl—Pyd— | I2-26 |
| —Phe.2$CH_3$—$CH_2CH_2$—Phe— | I2-27 |
| —Phe.3$CH_3$—$CH_2CH_2$—Phe— | I2-28 |
| —Phe.2Cl—$CH_2CH_2$—Phe— | I2-29 |
| —Phe.3Cl—$CH_2CH_2$—Phe— | I2-30 |
| —Phe.2CN—$CH_2CH_2$—Phe— | I2-31 |
| —Phe.3CN—$CH_2CH_2$—Phe— | I2-32 |
| —Phe.2Cl3Cl—$CH_2CH_2$—Phe— | I2-33 |
| —Phe.2Cl3F—$CH_2CH_2$—Phe— | I2-34 |
| —Phe.2O$CH_0$—$CH_2CH_2$—Phe— | I2-35 |
| —Phe.2O$CF_3$—$CH_2CH_2$—Phe— | I2-36 |
| —Phe.3O$CH_3$—$CH_2CH_2$—Phe— | I2-37 |
| —Phe.2$C_2H_5$—$CH_2CH_2$—Phe— | I2-38 |
| —Phe.2$C_2H_5$—$CH_2CH_2$—Phe— | I2-39 |
| —Phe.2$CF_3$—$CH_2CH_2$—Phe— | I2-40 |
| —Phe.3$CF_3$—$CH_2CH_2$—Phe— | I2-41 |

The 3-ring compounds according to formula I3 preferably exhibit the following structures for —$A^1$—$Z^1$—A1—$Z^1$—$A^2$:

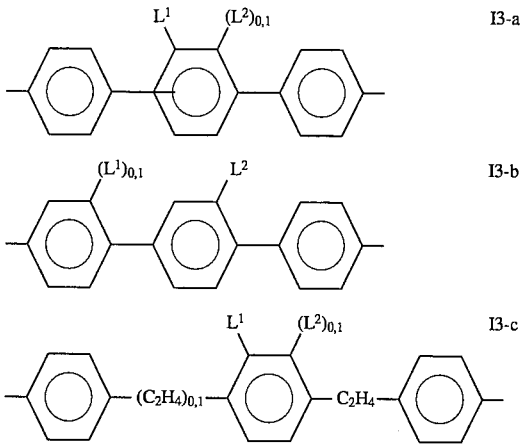

In these structures I3-a, I3-b and I3-c, $L^1$ and $L^2$ denote independently from each other —Cl, —F, —CN and —W—$C_rH_{2r+1-s}$ and, in particular, —Cl, —F, —CN, —$CH_3$, —$OCH_3$, —$CH_2F$, —$OCH_2F$, —$CHF_2$, —$OCHF_2$, —$CF_3$, —$OCF_3$ and/or —$C_2H_5$.

$(L^1)_{0,1}$ denotes that the $(L^1)$ substituent is absent or is present one time, $(L^2)_{0,1}$ denotes that the $(L^2)$ substituent is absent or is present one time, $(C_2H_4)_{0,1}$ denotes that the $(C_2H_4)$ substituent is absent or is present one time.

Especially preferred are the following patterns:

| | |
|---|---|
| —Phe—Phe.2$CH_3$—Phe— | I3-a-1 |
| —Phe—Phe.2Cl—Phe— | I3-a-2 |
| —Phe—Phe.2CN—Phe— | I3-a-3 |
| —Phe—Phe.2$CF_3$—Phe— | I3-a-4 |
| —Phe—Phe.2O$CF_3$—Phe— | I3-a-5 |
| —Phe—Phe.2O$CH_3$—Phe— | I3-a-6 |
| —Phe—Phe.2$C_2H_5$—Phe— | I3-a-7 |
| —Phe—Phe.2$CH_3$F—Phe— | I3-a-8 |
| —Phe—Phe.2Cl3F—Phe— | I3-a-9 |
| —Phe—Phe.2Cl3Cl—Phe— | I3-a-10 |
| —Phe—Phe.2$F_3CF_3$—Phe— | I3-a-11 |
| —Phe—Phe.3$CH_3$—Phe— | I3-b-1 |
| —Phe—Phe.3Cl—Phe— | I3-b-2 |
| —Phe—Phe.3CN—Phe— | I3-b-3 |
| —Phe—Phe.3$CF_3$—Phe— | I3-b-4 |
| —Phe—Phe.3O$CF_3$—Phe— | I3-b-5 |
| —Phe—Phe.3O$CH_3$—Phe— | I3-b-6 |
| —Phe—Phe.3$C_2H_5$—Phe— | I3-b-7 |
| —Phe.3F—Phe.3Cl—Phe— | I3-b-8 |
| —Phe.3F—Phe.3$CH_3$—Phe— | I3-b-9 |

| | |
|---|---|
| —Phe.3Cl—Phe.3Cl—Phe— | I3-b-10 |
| —Phe.3Cl—Phe.3CH$_3$—Phe— | I3-b-11 |
| —Phe—Phe.2Cl—Phe.3Cl— | I3-b-12 |
| —Phe—Phe.3Cl—Phe.3Cl— | I3-b-13 |
| —Phe—Phe.2Cl—Phe.2Cl— | I3-b-14 |
| —Phe—Phe.3Cl—Phe.2Cl— | I3-b-15 |
| —Phe—Phe.2CH$_3$—Phe.3Cl— | I3-b-16 |
| —Phe—Phe.3CH$_3$—Phe.3Cl— | I3-b-17 |
| —Phe—Phe.2CH$_3$—Phe.2Cl— | I3-b-18 |
| —Phe—Phe.3CH$_3$—Phe.2Cl— | I3-b-19 |
| —Phe—Phe.2F—Phe.3Cl— | I3-b-20 |
| —Phe—Phe.3F—Phe.3Cl— | I3-b-21 |
| —Phe—Phe.2F—Phe.2Cl— | I3-b-22 |
| —Phe—Phe.3F—Phe.2Cl— | I3-b-23 |
| —Phe—Phe.2Cl—Phe.3CN— | I3-b-24 |
| —Phe—Phe.3Cl—Phe.3CN— | I3-b-25 |
| —Phe—Phe.2Cl—Phe.2CN— | I3-b-26 |
| —Phe—Phe.3Cl—Phe.2CN— | I3-b-27 |
| —Phe—Phe.2CH$_3$—Phe.3CN— | I3-b-28 |
| —Phe—Phe.3CH$_3$—Phe.3CN— | I3-b-29 |
| —Phe—Phe.2CH$_3$—Phe.2CN— | I3-b-30 |
| —Phe—Phe.3CH$_3$—Phe.2CN— | I3-b-31 |
| —Phe—Phe.3F—Phe.3CN— | I3-b-32 |
| —Phe—Phe.2F—Phe.3CN— | I3-b-33 |
| —Phe—Phe.3F—Phe.2CN— | I3-b-34 |
| —Phe—Phe.2F—Phe.2CN— | I3-b-35 |
| —Phe—Phe.2CH$_3$—C$_2$H$_4$—Phe— | I3-c-1 |
| —Phe—Phe.2Cl—C$_2$H$_4$—Phe— | I3-c-2 |
| —Phe—Phe.2CN—C$_2$H$_4$—Phe— | I3-c-3 |
| —Phe—Phe.2CHF$_2$—C$_2$H$_4$—Phe— | I3-c-4 |
| —Phe—Phe.2OCH$_3$—C$_2$H$_4$—Phe— | I3-c-5 |
| —Phe—Phe.2CF$_3$—C$_2$H$_4$—Phe— | I3-c-6 |
| —Phe—Phe.2OCF$_3$—C$_2$H$_4$—Phe— | I3-c-7 |
| —Phe—Phe.2C$_2$H$_5$—C$_2$H$_4$—Phe— | I3-c-8 |
| —Phe—Phe.2CH$_3$3F—C$_2$H$_4$—Phe— | I3-c-9 |
| —Phe—Phe.2Cl3F—C$_2$H$_4$—Phe— | I3-c-10 |
| —Phe—Phe.2Cl3Cl—C$_2$H$_4$—Phe— | I3-c-11 |
| —Phe—Phe.2F$_3$CF$_3$—C$_2$H$_4$—Phe— | I3-c-12 |
| —Phe—C$_2$H$_4$—Phe.2CH$_3$—C$_2$H$_4$—Phe— | I3-c-13 |
| —Phe—C$_2$H$_4$—Phe.2Cl—C$_2$H$_4$—Phe— | I3-c-14 |
| —Phe—C$_2$H$_4$—Phe.2CN—C$_2$H$_4$—Phe— | I3-c-15 |
| —Phe—C$_2$H$_4$—Phe.2OCH$_3$—C$_2$H$_4$—Phe— | I3-c-16 |
| —Phe—C$_2$H$_4$—Phe.2CF$_3$—C$_2$H$_4$—Phe— | I3-c-17 |
| —Phe—C$_2$H$_4$—Phe.2OCF$_3$—C$_2$H$_4$—Phe— | I3-c-18 |

It was observed that the stability of 3-ring compounds wherein one of the 2 groups $Z^1$ is —COO— or —OCO— while the other denotes a single bond, can be increased if the compound is laterally di- or higher substituted, particularly di-substituted by —Cl—, —F, —CN and/or —CH$_3$. Compounds of this type are preferred.

Especially preferred are further 3-ring compounds where both groups $Z^1$ are either —COO—, or —OCO— and at least two of the rings $A^1$, $A^{1'}$ and $A^2$ are at least mono substituted.

In the compounds of formula I, $R^1$ is CH$_2$=CW—COO—, CH$_2$=CH—,

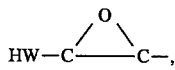

HWN—, HS—CH$_2$—(CH$_2$)$_m$—COO— with W being H, Cl or alkyl with 1–5 C atoms and m being 1–7.

Preferably, $R^1$ is a vinyl group, an acrylate group, an epoxy group, an amino group or a mercapto group, and especially preferred are the following meanings of $R^1$:

CH$_2$=CH—COO      $R^1$-1

     $R^1$-2

CH$_2$=C—COO      $R^1$-3
|
Cl

CH$_2$=CH—      $R^1$-4

H$_2$N—      $R^1$-5

H(alkyl)N—      $R^1$-6

HS—CH$_2$—(CH$_2$)$_m$—COO—      $R^1$-7

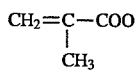
     $R^1$-8 with alkyl denoting C$_1$–C$_3$-alkyl and m being 1–5.

In the compounds of formula I, the spacer-type group P is alkylene with up to 12 C atoms, it also being possible for one or more non adjacent CH$_2$ groups to be replaced by O.

In case P is alkylene, P may be straight-chain or preferably. P especially preferably is ethylene, propylene, butylene, 1-methyl-propylene, 2-methyl- propylene, pentylene, 1-methyl-butylene, 2-methyl-butylene, hexylene, 2-ethyl-butylene, 1,3-dimethyl-butylene, heptylene, 1-methylhexylene, 2-methylhexylene, 3-methylhexylene, 4-methylhexylene, 5-methylhexylene, 6-methylhexylene, octylene, 3-ethyl-hexylene, nonylene, 1-methyloctylene, 2-methyloctylene, 7-methyloctylene, decylene, undecylene, 2-methyl-undecylene, 2,7,5-trimethyl-nonylene or 3-propyl-nonylene.

In case P is mono- or polyoxaalkylene, P may be straight chain or branched. In particular, P is 1-oxaethylene, 1-oxapropylene, 2-oxapropylene, 1-oxabutylene, 2-oxabutylene, 1,3-dioxabutylene, 1-oxa-pentylene, 2-oxa-pentylene, 3-oxy-pentylene, 2-oxa-3-methyl-butylene, 1-oxahexylene, 2- oxa-hexylene, 3-oxa-hexylene, 1,3-dioxa-hexylene, 1,4-dioxa-hexylene, 1,5- dioxa-hexylene, 1-oxa-heptylene, 2-oxa-heptylene, 1,3-dioxa-heptylene, 1,4-dioxaheptylene, 1,5-dioxaheptylene, 1,6-dioxaheptylene, 1,3,5-trioxaheptylene, 1-oxaoctylene, 2-oxaoctylene, 3-oxaoctylene, 4-oxaoctylene, 1,3-dioxaoctylene, 1,4-dioxanonylene, 1,4-dioxadecylene, 1,4-dioxa-undecylene and 1,3,5-trioxadodecylene.

X is —O—, —S—, —COO—, —OCO— or a single bond and in particular —O—, —COO—, —OCO— or a single bond. In case X is —O—, —S— or —COO—, the adjacent CH$_2$— group of Q is not replaced by —O—.

$Z^1$ is independently from each other —COO—, —OCO—, —CH$_2$CH$_2$— or a single bond and preferably —CH$_2$CH$_2$— or a single bond.

$R^2$ can be an alkyl radical with up to 15 C atoms which is unsubstituted, mono- or polysubstituted by halogen, it also being possible for one or more CH$_2$ groups in these radicals to be replaced, in each case independently from one another, by —O—, —S—, —CO—, —OCO—, —COO— or —O—COO— in such a manner that oxygen atoms are not linked directly to one another.

If $R^2$ is an alkyl radical or alkoxy radical, it may be straight-chain or branched. Preferably, it is straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy or octoxy, and furthermore methyl, nonyl, decyl, undecyl, dodecyl, tridecyl, tetradecyl, pentadecyl, methoxy, nonoxy, decoxy, undecoxy, dodecoxy, tridecoxy or tetradecoxy.

If $R^2$ is oxaalkyl, it is preferably straight-chain 2-oxapropyl (=methoxymethyl), 2-oxabutyl (=ethoxymethyl) or 3-oxabutyl (=2-methoxyethyl), 2-, 3- or 4-oxapentyl, 2-, 3-, 4- or 5-oxahexyl 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl.

Preferred branched radicals $R^2$ are isopropyl, 2-butyl (=1-methylpropyl), isobutyl (=2-methylpropyl), 2-methylbutyl, isopentyl, (=3-methylbutyl), 2 methylpentyl, 3-methylpentyl, 2-ethylhexyl 2-propylpentyl, 2-octyl isopropoxy, 2-methylpropoxy, 2-methylbutoxy, 3-methylbutoxy, 2-methyl pentoxy, 3-methyl-pentoxy, 2-ethylhexoxy, 1-methylhexoxy, 2-octyloxy, 2-oxa-3-methylbutyl, 3-oxa-4-methylpentyl, 4-methylhexyl, 2-nonyl, 2-decyl, 2-dodecyl, 6-methyloctoxy, 6-methyloctanoyloxy, 5-methylheptyloxy carbonyl, 2-methylbutyryloxy, 3-methylvaleryloxy, 4-methylhexanoyloxy, 2-chloropropionyloxy, 2-chloro-3-methylbutyryloxy, 2-chloro-4-methylvaleryloxy, 2-chloro-3-methylvaleryloxy, 2-methyl-3-oxypentyl, 2-methyl-3 -oxahexyl.

$R^2$ can also be a polar terminal group and in particular —CN, —Cl or F; $R^2$ can also be —(L)—$C_dH_eF_{2d+1-e}$ wherein L is a single bond, —O— or —S—, d is 1 or 2 and e is 0, 1, 2, 3, 4 or 5.

$R^2$ can also have one of the meanings given for $R^1$—Q—X— above. In case $R^2$ is an optionally substituted alkyl radical, $R^1$ preferable is a vinyl or acrylate group while in case $R^2$ is $R^1$—Q—X all meanings given above for $R^1$ are preferred.

Reactive liquid crystalline compounds exhibiting two reactive groups R which can be chosen independently from each other, are preferred; especially preferred are compounds exhibiting two identical reactive groups.

The reactive liquid crystalline compounds according to formula I and according to the preferred subclasses can be prepared by methods which are known per se and which are described, for example, in standard works of organic chemistry such as, for example, Houben-Weyl, Methoden der Organischen Chemie, Thieme-Verlag, Stuttgart. Some specific methods can be taken from the examples.

Methods to introduce the reactive group $R^1$ as a substituent are well-known in literature. A preferred method to introduce an acrylate group as a terminal substituent into a rod-like molecule is described in examples 1–3.

Terminal vinyl ether groups can be introduced, for example, by transetherification reactions. The alcohols are treated with butylvinyl ether in dichloromethane in the presence of 1,10-phenanthroline palladium (II) diacetate as is described in V. Perec, M. Lee and H. Jonsson, J. Polym. Sci. Part A, 1991, 29, 327–337.

A thiol group can be introduced, for example, by converting an aliphatic alcohol into a thiol; see, for example, Lucien and Nouveau, J. Chem., 1979, i, 15.

The "ene" group can be introduced by directly alkylating the core with a suitable ω-bromo-α-alkene.

The reaction methods mentioned are briefly summarized in the following synthetic tree:

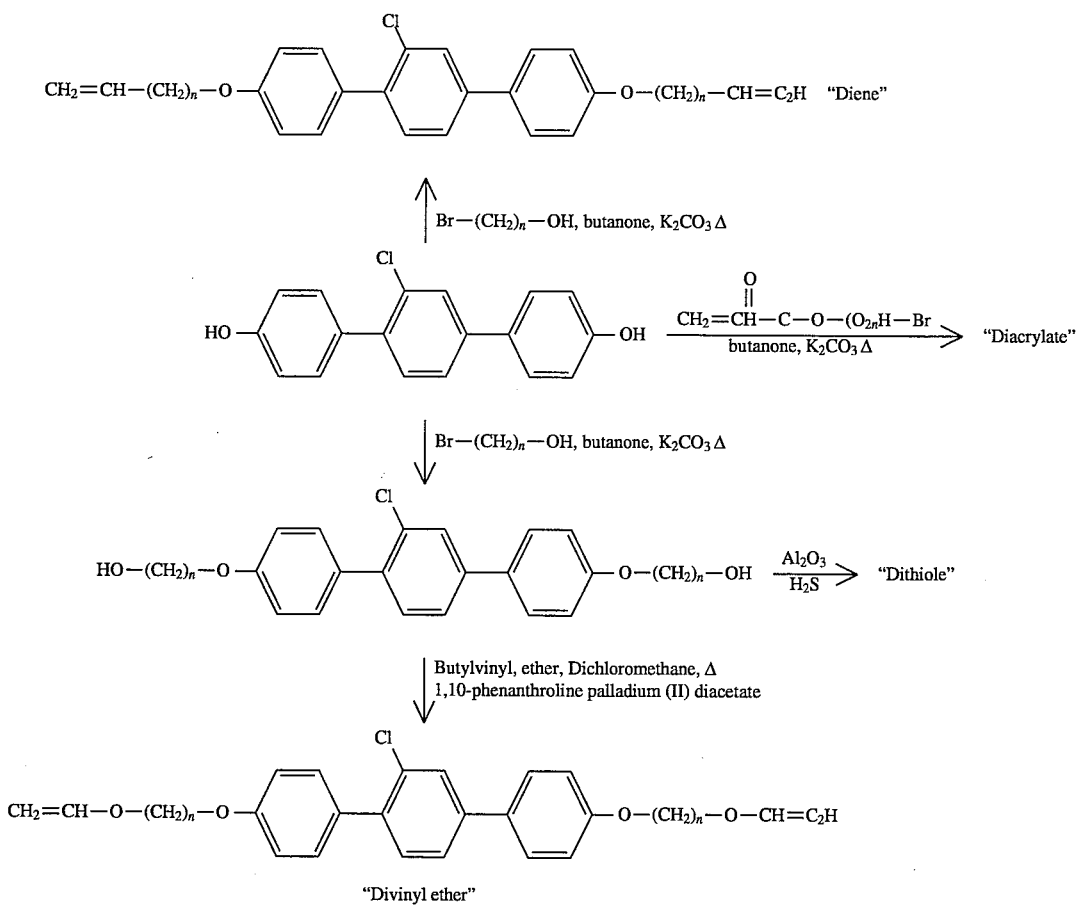

The reaction schemes mentioned above are to illustrate the invention without restricting it. The expert can choose other reaction methods without any inventive efforts.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding European application 93116679.7, filed Oct. 15, 1993, is hereby incorporated by reference.

EXAMPLES

Example 1

The reactive liquid crystalline compound (1)

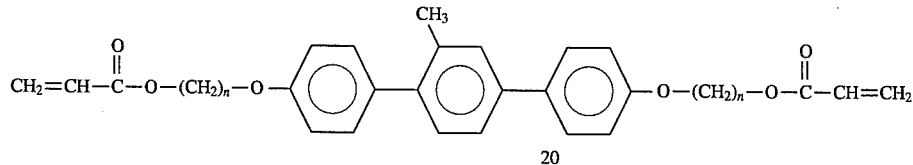

is prepared via the sequence of reaction steps shown in diagram 1.

Compound (1) exhibits the following phase sequence:
n=3: K 73 N 80 I
n=6: K 69 $S_A$ 75 N 78.6 I Example 2

The reactive liquid crystalline compound (2)

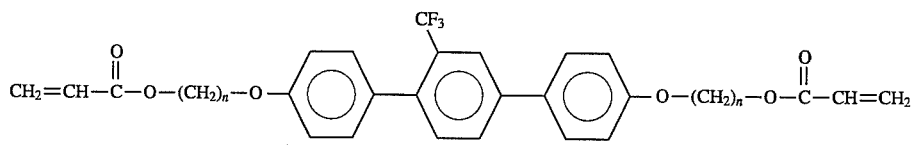

is prepared via the sequence of reaction steps shown in diagram 2.

Example 3

The reactive liquid crystalline compound (3)

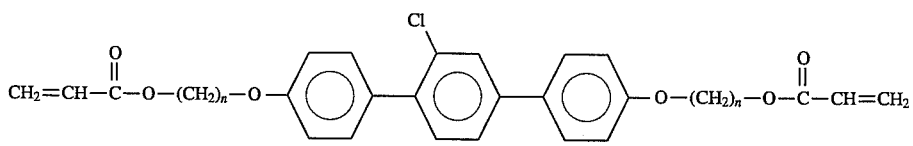

is prepared via the sequence of reaction steps shown in diagram 3.

Compound (3) exhibits the following phase sequence:
n=3: K 84.6 (S 34.8 N 70.8) I
n=4: K 53.4 S 65.3 N 73.4 I
n=5: K 63.9 (S 52) N 84.1 I
n=6: K 47.9 S68 N 78.7 I Example 4

The reactive liquid crystalline compound (4)

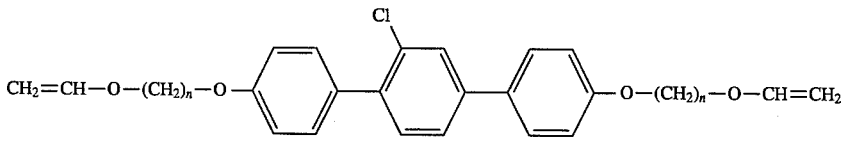

is prepared by reacting the compound obtained in step 3 of diagram 3 according to diagram 4.

Compound (4) exhibits the following phase sequence:
n=3: K 60.5 (S 6.2N 30.45) I
n=4: K 85.8 N 121.4 I
n=5: K 60.7 S 47.3) N 72.6 I
n=6: K 69.9 S 76.2 N 104.9 I Example 5

The reactive liquid crystalline compound (5)

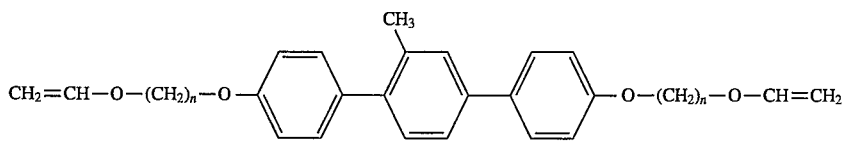

is prepared by reacting ie compound obtained in step 3 of diagram 1 according to diagram 4.

Compound (5) exhibits the following phase sequence.

n=3: K 74.4 (S 37.7 N 52.6) I
n=6: K 79.4 S 89.6 N 111.4 I

Example 6

The reactive liquid crystal compound (6)

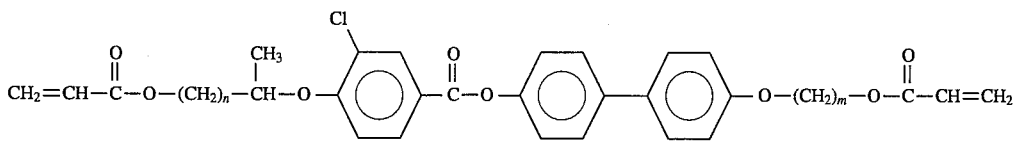

is prepared via the sequence of reaction steps shown in diagram 5.

Compound (6) exhibits the following phase sequence.

n=3, m=6: K 50.1 (Sc 41.9) $S_A$ 70.6 I

Example 7

The reactive liquid crystal compound (7)

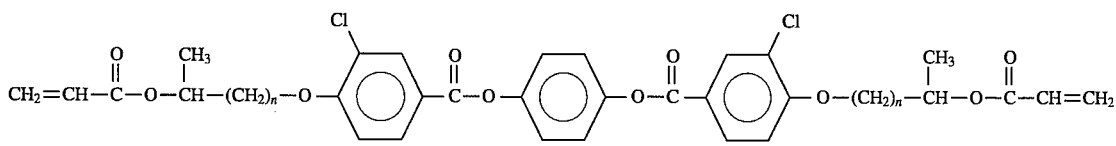

is prepared via the sequence of reaction steps shown in diagram 6.

Compound (7) exhibits the following phase sequence.

n=3: K 131.5 I

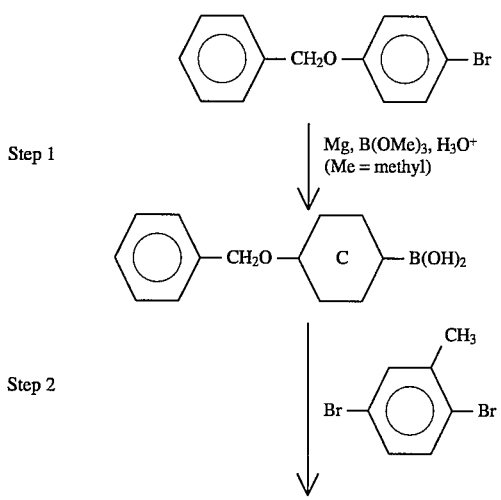

Diagram 1

-continued
Diagram 1
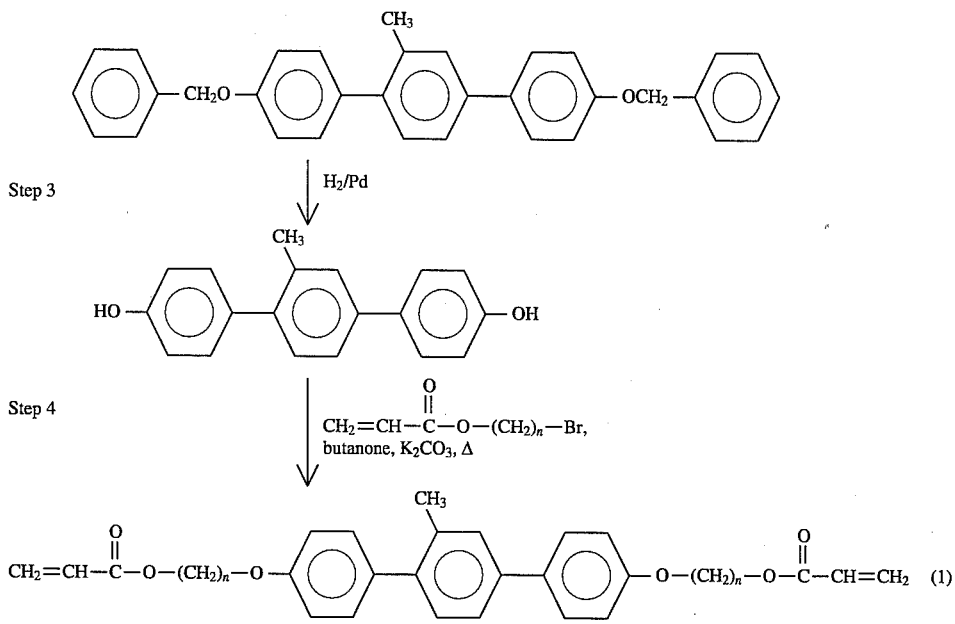
Diagram 2
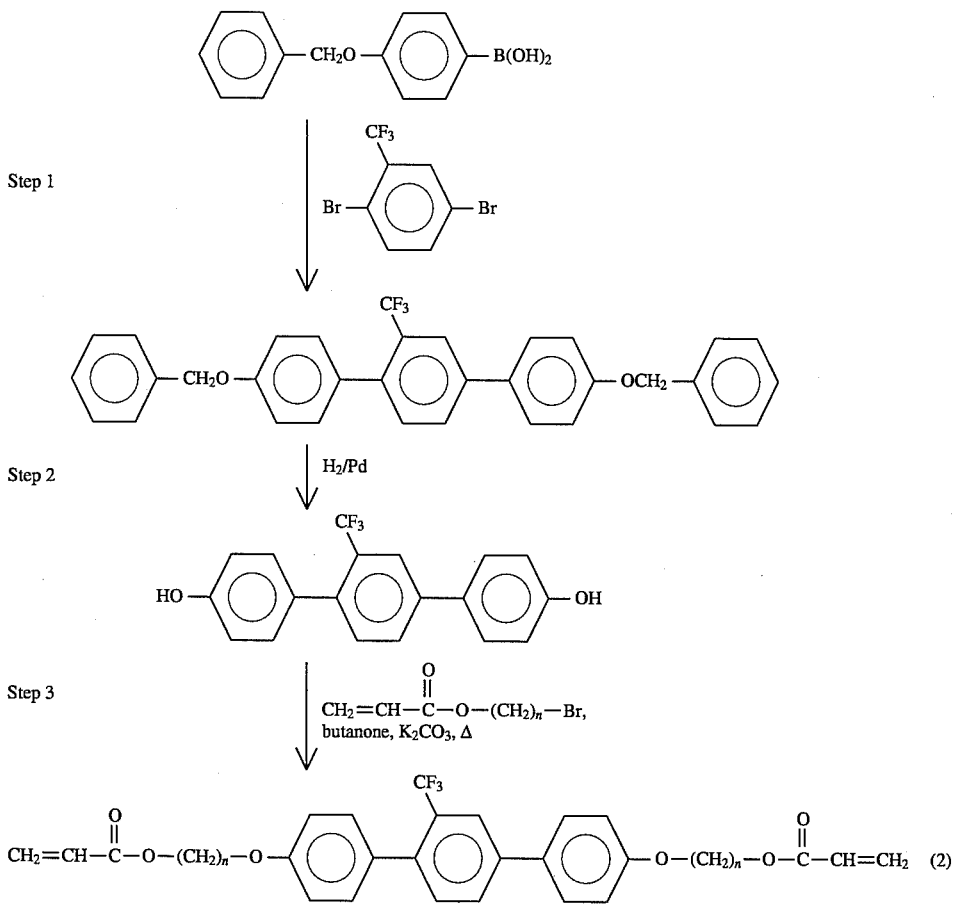

5,622,648
Diagram 3
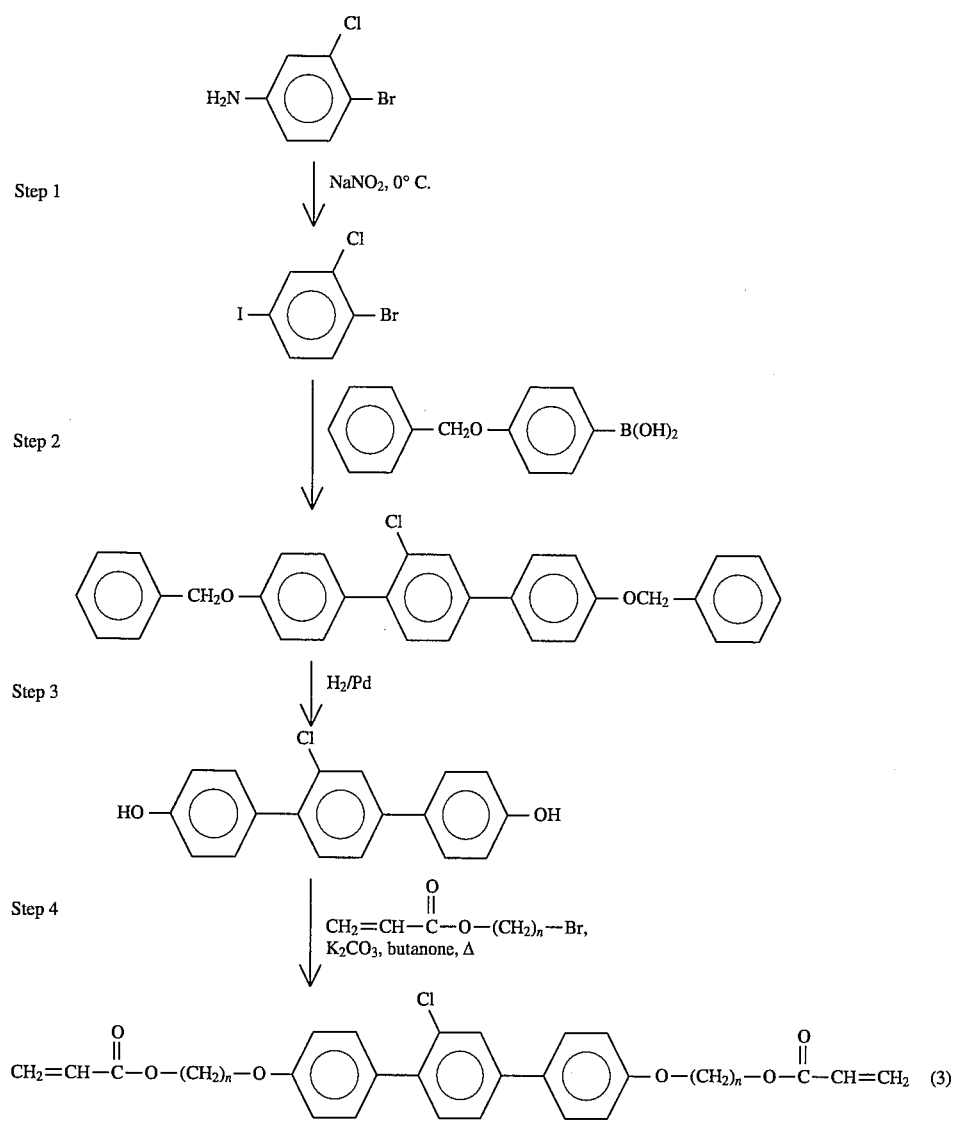

Diagram 4
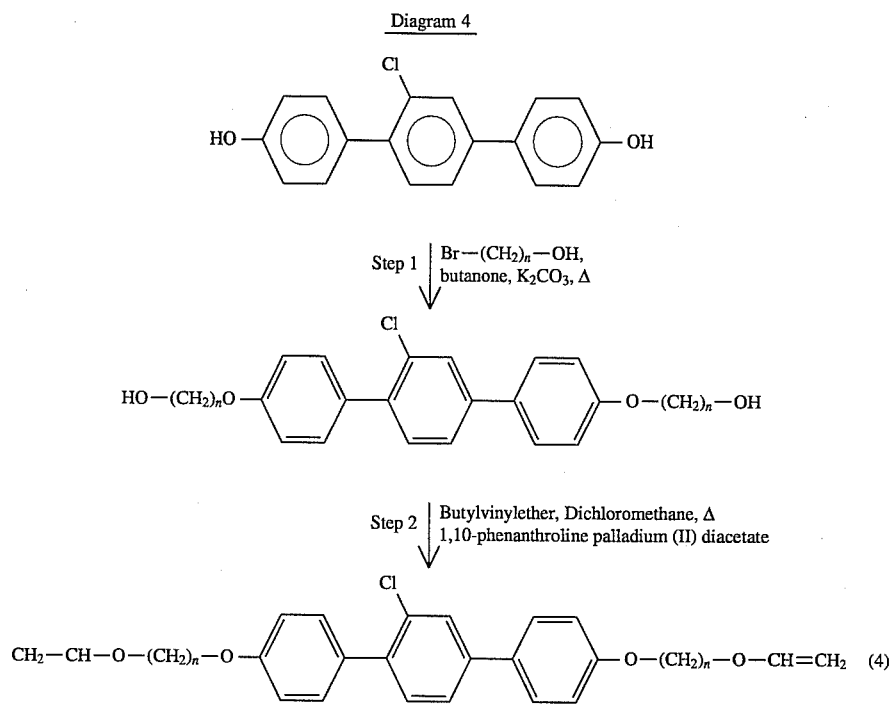
Diagram 5
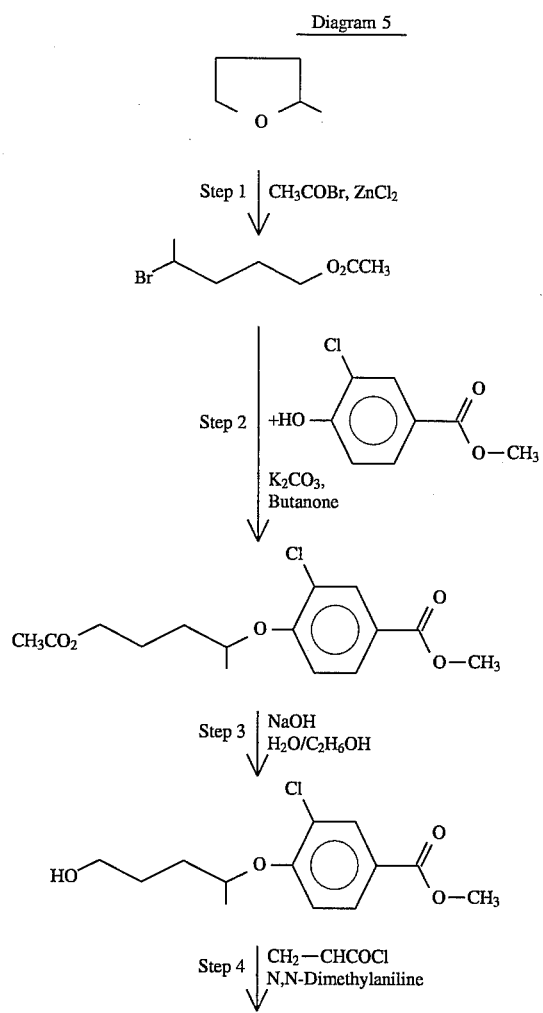

-continued
Diagram 5
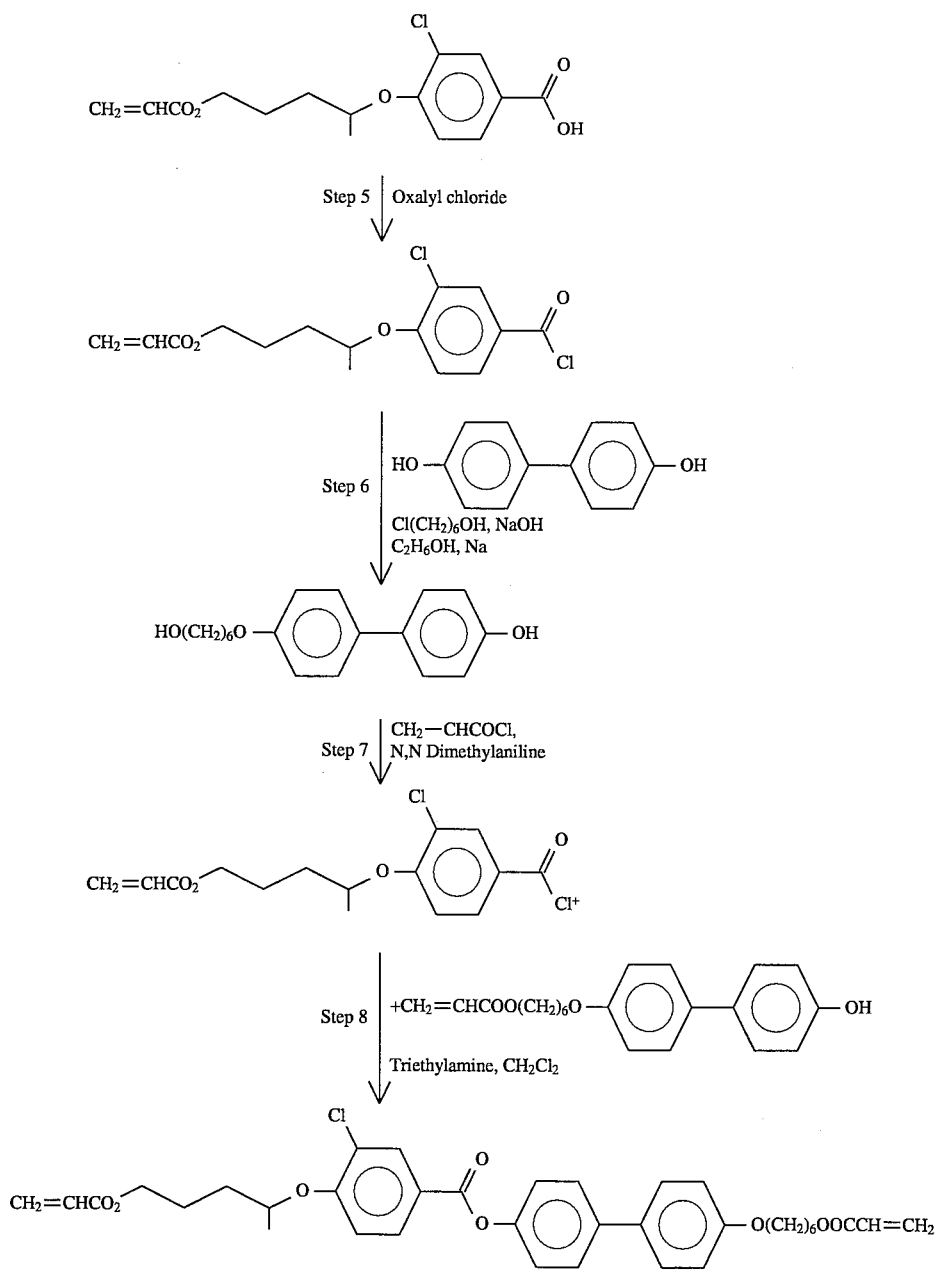
Diagram 6
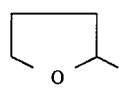
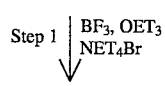

-continued
Diagram 6
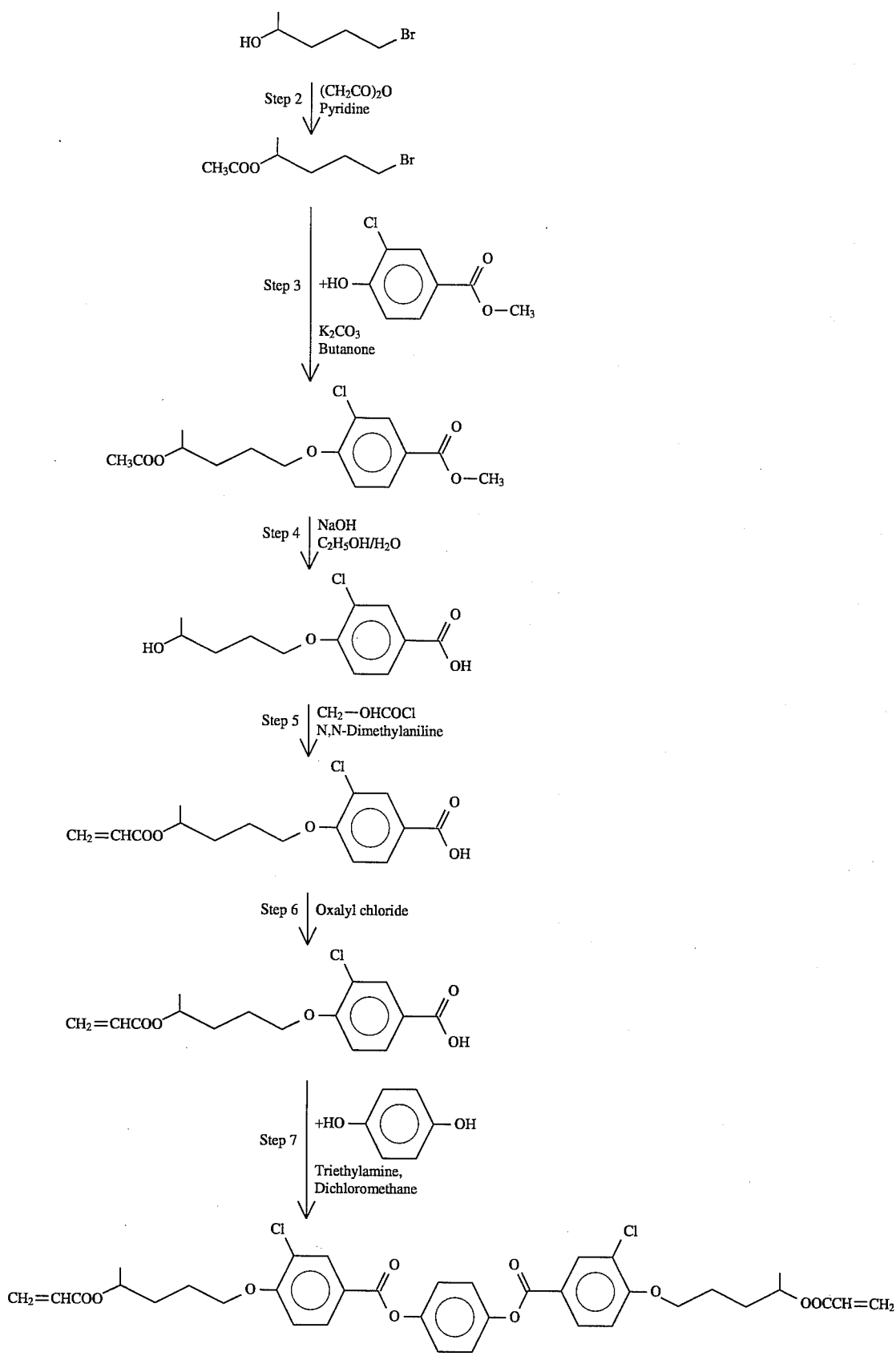

What is claimed is:
1. A reactive liquid crystal compound of formula I

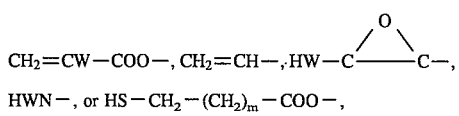

wherein
$R^1$ is

$HWN-$, or $HS-CH_2-(CH_2)_m-COO-$,

W is H, Cl or $C_{1-5}$-alkyl,
m is 1–7,
P is alkylene with up to 12 C atoms, one or more $CH_2$ groups optionally being replaced by O in such a manner that oxygen atoms are not directly linked to one another;
X is $-O-$, $-S-$, $-COO-$, $-OCO-$ or a single bond,
$R^2$ has one of the meanings of $R^1-P-X$,
n is 1 or 2,
$A^1$, $A^2$ are independently 1,4-phenylene which is unsubstituted or mono- or polysubstituted by F, Cl or $-W-C_rH_sF_{2r+1-s}$, or one of $A^1$ or $A^2$ is

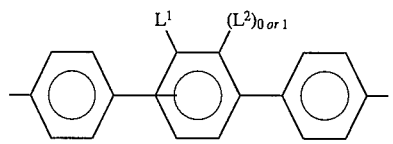

pyridine-2,5-diyl or pyrimidine-2,5 diyl,
$Z^1$ is each independently $-CO-O-$, $-O-CO-$, $-CH_2CH_2-$ or a single bond,
r is 1 or 2,
s is 0, 1, 2 or 3 if r is 1 and 0, 1, 2, 3, 4, or 5 if r is 2,
W is a single bond, $-O-$, $-S-$ or $-CO-$,
where n=2 both the moieties $A^1$ and both the moieties $Z^1$ are independently as defined above,
with the provisos (i) that at least one of $A^1$ and $A^2$ is a 1,4-phenylene group which is mono-or polysubstituted by Cl or $-W-C_rH_sF_{2r+1-s}$, said 1,4-phenylene group optionally additionally substituted by one or more F-atoms, and (ii) if n=2 (a) only one of $Z^1$ is $-COO-$ or $-OCO-$ or (b) at least one of $A^1$ and $A^2$ is substituted twice or (c) at least two of $A^1$ and $A^2$ are substituted.

2. A reactive liquid crystal compound according to claim 1 wherein $-A^1-Z^1-A^1-Z^1-A^2-$ is

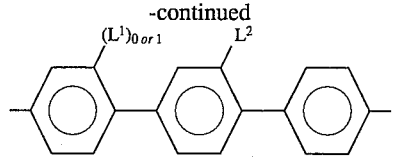

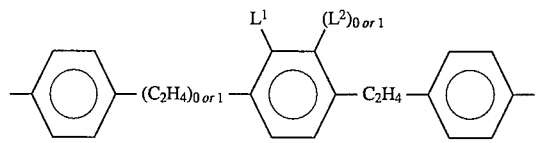

wherein
$L^1$ and
$L^2$ are F, $-Cl$ or $-W-C_rH_sF_{2r+1-s}$, and
W is a single bond, $-O-$, $-S-$ or $-CO-$.

3. A reactive liquid crystal compound according to claim 1 wherein $A^1-Z^1-A^1-Z^1-A^2-$ is

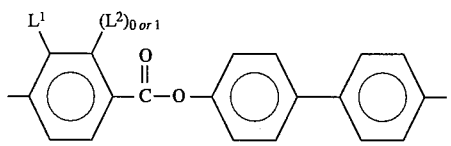

wherein
$L^1$ and
$L^2$ are F, $-Cl$ or $-W-C_rH_sF_{2r+1-s}$ and
W is a single bond, $-O-$, $-S-$ or $-CO-$.

4. A reactive liquid crystal compound according to claim 1 wherein $-A^1-Z^1-A^1-Z^1-A^2-$ is

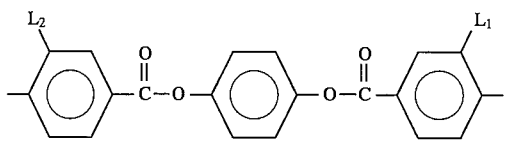

wherein
$L^1$ and
$L^2$ are each independently F, $-Cl$ or $-W-C_rH_sF_{2r+1-s}$ and
W is a single bond, $-O-$, $-S-$ or $-CO-$.

5. A liquid crystalline phase comprising at least two liquid crystalline compounds, wherein at least one compound is a compound according to claim 1.

6. An electrooptical device containing a liquid crystalline phase, wherein the phase is one according to claim 5.

7. An electrooptical scattering system containing a liquid crystalline phase, wherein the phase is one according to claim 5.

8. An oriented liquid crystal polymer containing a liquid crystalline phase, wherein the phase is one according to claim 5.

* * * * *